United States Patent [19]

Kelemen et al.

[11] Patent Number: 5,026,640

[45] Date of Patent: Jun. 25, 1991

[54] PROCESS FOR THE CONVERSION OF CORRINOIDS PRODUCED BY MICROORGANISMS INTO CYANOCORRINOIDS

[75] Inventors: Ágnes Kelemen; Éva Cserey Pechány; István Jaksa, all of Budapest, Hungary

[73] Assignee: Richter Gedeon Vegyeszeti Gyar Rt, Budapest, Hungary

[21] Appl. No.: 657,748

[22] Filed: Oct. 4, 1984

[30] Foreign Application Priority Data

Oct. 4, 1983 [HU] Hungary ................ 3440/83

[51] Int. Cl.$^5$ .............. C12P 19/42; C12P 19/28; C07H 23/00
[52] U.S. Cl. ........................ 435/86; 435/85; 536/25
[58] Field of Search ........... 435/85, 86; 536/25

[56] References Cited

U.S. PATENT DOCUMENTS

| | | | |
|---|---|---|---|
| 3,037,016 | 5/1962 | Barker | 435/86 |
| 3,115,489 | 12/1963 | Cords et al. | 435/86 |
| 3,163,637 | 12/1964 | Chaiet | 435/86 |
| 3,846,237 | 11/1974 | Toohey | 435/86 |

*Primary Examiner*—Elizabeth C. Weimar
*Assistant Examiner*—Gail Poulos
*Attorney, Agent, or Firm*—Herbert Dubno; Jonathan Myers

[57] ABSTRACT

The invention relates to a process for the conversion of corrinoids produced by microorganisms into cyanocorrinoids by reaction with cyanides. According to the invention a fermentation broth obtained by disruption of microorganism cells in a known manner, preferably by heat treatment in the presence or absence of sulfite ions, optionally after purification steps known per se, is contacted with a suitable adsorbent or ion exchange resin, the corrinoids adsorbed on the surface of the adsorbent or ion exchange resin are treated with an aqueous solution containing cyanide ions or a compound capable of supplying cyanide ions, in an amount providing cyanide ions in a 1.1 to 2.0-fold molar excess related to the corrinoids, the adsorbent or ion exchange resin is washed with water, and the cyanocorrinoids obtained is eluted in a known manner, preferably with aqueous ethanol.

4 Claims, No Drawings

PROCESS FOR THE CONVERSION OF CORRINOIDS PRODUCED BY MICROORGANISMS INTO CYANOCORRINOIDS

The invention relates to a new process for the conversion of corrinoids produced by microorganisms into cyanocorrinoids.

Corrinoids are known to be produced exclusively by microorganisms. In microorganism cells corrinoids are accumulated in the form of coenzymes or are bound to proteins. As a first step of the isolation of corrinoids the cells have to be disrupted and the bonds between the desoxyadenosyl group of the coenzyme $B_{12}$ corrine skeleton and the proteins should be broken [Ullmann: Encyklopedie der Chemischen Technology, 18, 214 (1967)]. If the cells are disrupted in the presence of cyanide, sulfite or nitrite ions, the coenzymes are converted into the corresponding cyano-, sulfito-or nitritocorrinoids, while in the absence of the above-mentioned ions hydroxycorrinoids are obtained. It is well known that the stability of corrinoid complexes is different. The stabilities are decreased in the following order: cyano-, sulfito-, nitrito-, hydroxycorrinoids. Since hydroxycorrinoids are extremely unstable, in the hitherto known processes they were converted into the more stable cyano- or sulfitocorrinoids already in the first step of processing. The stable cyanocorrinoids were generally prepared by disrupting the microorganism cells in the presence of cyanide ions.

The processes known in the art for the disruption of cells, liberation of corrinoids from the proteinbounded form and their conversion into the corresponding cyanocorrinoids are summarized e.g. in the following monographies: E. L. Smith: Vitamin $B_{12}$ Ed. Methuen's, 15, 26–28 (1965); Pawelkiewicz: Vitamin $B_{12}$ und Intrinsic Factor, Enke Verlag Stuttgart, 280 (1962); W. Friedrich: Vitamin $B_{12}$ und verwandte Corrinoide (R. Ammon: Fermente, Hormone, Vitamine III/2) 10–13, G. Thieme Verlag, Stuttgart (1975).

Since as an end product cyanocorrinoids are to be prepared, due to the high volumes involved and the presence of impurities which may also react with the cyanide ions, during the industrial preparation of cyanocorrinoids cyanide ions have to be employed in a multiple excess related to the hydroxycorrinoids to obtain the desired end product. This causes safety and environmental problems.

According to the Hungarian patent specification No. 171,339 during the disruption of cells and the liberation of corrinoids from the protein bonds the cyanide ion is employed in a 100 to 600-fold, preferably 200 to 400-fold molar excess related to the vitamin $B_{12}$ content of the fermentation broth. The fermentation broth is treated with the cyanide ions for 10 to 300, preferably 20 to 120 minutes.

According to the U.S. Pat. No. 2,530,416 the fermentation broth obtained by cultivation of vitamin $B_{12}$-producing microorganisms or a concentrate obtained therefrom is treated with a compound capable of supplying cyanide ions, e.g. a cyanohydrogen salt capable of ionic dissociation.

In the process disclosed in the French patent specification No. 2,209,842 Propionibacterium cells are disrupted in the presence of 5% of sodium metabisulfite, at 60° to 70° C. The sulfitocorrinoids obtained are first purified by solvent extraction and then treated to the vitamin $B_{12}$ content, at 60° C. for 15 minutes, to obtain the desired cyanocorrinoids. The product obtained after crystallization from acetone contains 10 ppm of free cyanide ions.

A common disadvantage of the known processes is that they require an extremely high amount of cyanide ions when used on an industrial scale. Therefore, for industrial realization difficult safety and environmental protection problems must solved. A further drawback is that the crude product contains free cyanide ions. This is no problem if crystalline corrinoids are prepared, since this impurity can be eliminated from the corrinoids during the purification steps. If, however, the crude product is to be used as a fodder additive, the free cyanide ion concentration should be kept under a certain limit.

By the process according to the invention the stable cyanocorrinods are prepared without the above disadvantages. The main steps of the process are as follows:

The disruption of microorganism cells and the liberation of the corrinoids from the protein bonds are carried out in a known manner, in the presence or absence of sulfite ions and/or by heat treatment, whereupon the corrinoids present in the solution are adsorbed on an adsorbent or cation exchange resin, optionally after known purification steps. By the adsorption step the hydroxo- or sulfitocorrinoids are stabilized. Stable cyanocorrinods are then prepared from the corrinoids adsorbed on the surface of the adsorbent or ion exchange resin by treating the adsorbent or resin with a 1.1 to 2.0 molar excess of cyanide ions or a compounds capable of supplying cyanide ions, e.g. a cyanohydrine. This reaction takes place instantanously on the surface of the adsorbent or cation exchange resin. The unreacted excess of cyanide ions can be eliminated by washing the adsorbent or cation exchange resin, therefore, the cyanocorrinoids eliminated from the adsorbent or cation exchange resin are devoid of free cyanide ions.

The invention relates to a new process for the conversion of corrinoids produced by microorganisms into cyanocorrinoids, in which a fermentation broth obtained by the disruption of cells in a known manner, preferably by heat treatment in the presence or absence of sulfite ions (optionally after purification steps known per se), is contacted with a suitable adsorbent or ion exchange resin and the corrinoids adsorbed on the surface of the adsorbent or resin are then treated with an aqueous solution containing cyanide ions or a compound capable of supplying cyanide ions, in an amount providing cyanide ions in a 1.1 to 2.0 molar excess related to the corrinoids. The adsorbent or ion exchange resin is then washed with water and the cyanocorrinoids formed are eluted in a known manner, preferably with aqueous ethanol.

The process according to the invention can advantageously be used also for the treatment of fermentation broths obtained by disrupting the cells by heat treatment in the absence of sulfite ions. In this case the corrinoids present in the unfiltered fermentation broth are directly adsorbed on a macroreticular adsorption resin, using fluidized bed techniques or by simple admixture. Since this step can be accomplished in an extremely short time, the hydroxycorrinoids are practically not decomposed during this period. The corrinoids bound to the adsorbent are then converted into cyanocorrinoids by a dilute aqueous solution containing cyanide ions in a 1.1 to 2.0 molar excess related to the adsorbed corrinoids, whereupon the unreacted cyanide ions are washed off with water and the cyanocorrinoids are eluted from the adsorbent in a known manner. The solution obtained contains the total corrinoid amount in a stable cyanide form and is practically devoid of free cyanide ions.

The main advantages of the new process according to the invention are as follows:

(1) The amount of cyanide ions required for the reaction is two orders of magnitude lower than in the hitherto known processes.

(2) The process is particularly suitable for economic industrial realization since:

the adsorption and purification of the active ingredient and its conversion into cyanocorrinoid and elution can be carried out in a continuous operation with a good yield;

there is no need of expensive processes and equipments for the elimination of cyanide ions;

the order of technological steps meets the safety requirements, since the possibility of hydrogen cyanide evolution is excluded as the cyanocorrinoids are preapred at a neutral pH.

(3) The product eluted from the adsorbent is practically devoid of free cyanide ions. This is particularly important if the product is to be employed as a fodder additive, without further purification.

(4) In the waste water obtained during the realization of the process, which is discharged into the sewage system or living waters the cyanide ion concentration is under the permitted limits, therefore the requirements of the environmental protection are met.

Further details of the invention will now be illustrated by the following non-limiting Examples.

EXAMPLE 1

1 m³ of a fermentation broth obtained by fermentation (Hungarian patent specification No. 159,356) with a methane-producing mixed micropopulation containing Corynebacterium sp. (24A1), Corynebacterium sp. (244C1), Lactobacillus sp. (244B C1) and Propionibacterium sp. (239 A1/6), deposited in the Hungarian National Collection of Microorganisms (OKI) under Nos. 71, 77, 78 and 79, respectively, having a pH of 6.3 and containing 50 g of corrinoids, is adjusted to pH 4.0 with sulfuric acid. The fermentation broth is then heated up to 100° C. and kept at this temperature for 10 minutes. During this step the cells are disrupted and the corrinoids set free from the cells are dissolved in the fermentation medium. The solution contains 24 g of hydroxycobalamine and 23.5 g of related corrinoids. The fermentation broth is passed through a column filled with 20 lit. of DIAION HP 20 (Mitsubishi) macroreticular adsorption resin in upwards direction, by fluidized bed technology. In this step corrinoids in the fermentation broth are adsorbed on the resin. The cell debris and the organic and inorganic impurities are then eliminated by passing water through the column in the same direction as during adsorption. Thereafter, 20 lit. of an aqueous solution containing altogether 3.0 g of potassium cyanide (1.25 equivalents) are introduced into the column in upwards direction. After standing for 10 minutes the potassium cyanide-containing water is discharged from the system, and the column is washed through with 100 lit. of water. The solution used for cyanide treatment and eliminated from the column is combined with the aqueous washing liquor. The 120 lit. solution obtained contains 0.15 mg of free cyanide ions pro liter.

Cyanocorrinoids are eluted from the adsorption resin with 100 lit. of methanol, passed continuosly downwards. From the methanolic eluate methanol is evaporated in vacuum, at a temperature not exceeding 50° C. The aqueous solution contains 20.5 g of cyanocobalamine and 20.0 g of other cyanocorrinoids. According to HPLC analysis the hydroxycobalamine concentration of the product is below 0.5%. Free cyanide ions cannot be detected even in traces. After drying, the product can be utilized as a fodder additive.

EXAMPLE 2

As a starting material 100 lit. of a fermentation broth obtained as described in Example 1 (using the same microorganisms) containing 5.0 g of corrinoids is employed. For disruption of cells 0.86 kg of disodium hydrogen-phosphate. 2H₂0, 1.1 kg of citric acid and 1.0 kg of sodium metabisulfite are added to the fermentation broth, which is then kept in an autoclave at 120° C. for 10 minutes. The mixture obtained contains 2.3 g of sulfitocobalamine and 2.42 g of related sulfitocorrinoids. After cooling the mixture is passed upwards through a column filled with 3 lit. of Amberlite XAD 2 (Rohm and Haas) macroreticular adsorption resin. The sulfitocorrinoids are adsorbed on the adsorption resin. The traces of fermentation broth are eliminated from the resin column with water passed upwards through the column. Thereafter 15 lit. of an aqueous solution containing 0.5 g of potassium cyanide (2 equivalents) are passed downwards through the column at a rate of 2 bed volumes/hour. As a result, the characteristic yellowish-red colour of sulfitocorrinoids turns to bright purplish characteristic of cyanocorrinoids. After the aqueous potassium cyanide solution 45 lit. of water are passed downwards through the column, to eliminate cyanide ions. The liquor passing out is combined with the aqueous washing liquor. The free cyanide ion content of the combined liquor amounts to 0.12 mg/lit. Corrinoids are eluted from the resin column with 10 lit. of a 80 vol/vol % aqueous methanol solution. The methanolic eluate is evaporated in vacuum to eliminate methanol. The aqueous solution obtained contains 1.92 g of cyanocobalamine and 2.01 g of related cyanocorrinoids. By HPLC no sulfito- or hydroxycorrinoid can be detected. The product is devoid also from free cyanide ions.

EXAMPLE 3

From 100 lit. of a fermentation broth obtained by aseptic fermentation with Propionibacterium sp. (A1/6) deposited at the Hungarian National Collection of Microorganisms (OKI) under No. 239 cells containing corrinoids are separated. The total corrinoid content of the cell-cream (biomass) obtained is 7.5 g. To the biomass 20 lit. of water are added, its pH is adjusted to 4.0 with hydrochloric acid, and the mixture is kept at 120° C. for 10 minutes, in an autoclave. After cooling, the cell debris is eliminated by separation. The clear solution obtained contains 5.1 g of hydroxycobalamine and 2.4 g of other corrinoids. The solution is passed through 35 lit. of an Amberlite IRC 50 cation exchange resin, which is in a hydrogen cycle. The corrinoids present in the solution are adsorbed on the column. Thereafter the resin column is washed with 5 lit. of water, and subsequently 40 lit. of water containing 400 mg of sodium cyanide are passed through the column at a reate of 20 lit./hour. The column is then washed with water until the liquor passing out becomes cyanide ion-free. The washing liquor containing cyanide ions is collected; its free cyanide ion content amounts to 0.19 mg/lit. From the cation exchange column the cyanocorrinoids are eluted in a known manner, with a 80 vol./vol. % aqueous acetone solution. From the eluate acetone is evaporated in vacuum. The aqueous solution obtained contains 3.8 g of cyanocobalamine and 1.7 g of other cyanocorrinoids. By HPLC no hydroxycobalamine is detected in the solution. From the solution crystalline cyanocobalamine can be prepared in a known manner, e.g. by extraction with a 1:6 mixture of phenol and chloroform, dissolution of the active ingredient in water, and acetone treatment.

EXAMPLE 4

The procedure described in Example 3 is followed, except that from the solution obtained after disruption of cells and separation corrinoids are adsorbed on montmorillonite corresponding to 2% by weight, after adjusting the pH to 3.5. When the adsorption is complete, the adsorption clay is eliminated by filtration and washed to neutral with water. The adsorbent is then stirred with 10 lit. of a 40 mg/lit. aqueous sodium cyanide solution for 30 minutes, filtered and the adsorbent remaining on the filter is washed with 20 lit. of water. The corrinoids are then eluted from the adsorbent with a 60 vol./vol. % aqueous ethanol solution. From the eluate ethanol is eliminated by evaporation in vacuum. The aqueous solution obtained contains 3.5 g of cyanocobalamine and 1.6 g of other cyanocorrinoids.

We claim:

1. A process for converting microbiologically produced corrinoids to cyanocorrinoids practically devoid of free cyanide ions which comprises the steps of:
   (a) acidifying a fermentation broth containing corrinoids which are bound to microorganism cells to a pH of 4;
   (b) disrupting the cells in the fermentation broth containing corrinoids by heating to a temperature of 100° to 120° C. for 10 minutes to release the microorganism cells;
   (c) passing the fermentation broth whose microorganism cells were disrupted during step (b) through an adsorbent or cation exchange resin so that the corrinoids from the fermentation broth are adsorbed on the surface of the adsorbent or cation exchange resin;
   (d) converting the corrinoids adsorbed on the adsorbent or cation exchange resin to cyanocorrinoids by treating the corrinoids with an aqueous solution containing cyanide ions or a compound capable of supplying cyanide ions in a 1.1 to 2.0 molar ratio with respect to the corrinoids wherein the cyanide ions are present in excess;
   (e) washing the adsorbent or cation exchange resin with water;
   (f) eluting the cyanocorrinoids from the adsorbent or cation exchange resin by passing therethrough an eluant selected from the group consisting of methanol, ethanol and acetone, and recovering an eluate rich in cyanocorrinoids; and
   (g) evaporating the eluate to drive off the eluant and recovering the cyanocorrinoids.

2. The process for converting microbiologically produced corrinoids to cyanocorrinoids defined in claim 1 wherein the molar ratio between the cyanide ions and the corrinoids according to step (d) is 1.25.

3. The process for converting microbiologically produced corrinoids to cyanocorrinoids defined in claim 1 wherein the cyanide ions in step (d) are provided by potassium cyanide.

4. The process for converting microbiologically produced corrinoids to cyanocorrinoids defined in claim 1 wherein the cyanide ions in step (d) are provided by sodium cyanide.

* * * * *